US009011889B2

(12) United States Patent
Heinemann et al.

(10) Patent No.: US 9,011,889 B2
(45) Date of Patent: *Apr. 21, 2015

(54) INSECTICIDE-CONTAINING POLYMERIC MATERIAL

(75) Inventors: Maren Heinemann, Bergisch Galdbach (DE); Thomas Böcker, Leichlingen (DE); Karin Horn, Solingen (DE); Guenther Nentwig, Leverkusen (DE); Rainer Sonneck, Leverkusen (DE); Thomas König, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 1042 days.

This patent is subject to a terminal disclaimer.

(21) Appl. No.: 13/086,493

(22) Filed: Apr. 14, 2011

(65) Prior Publication Data

US 2011/0256195 A1    Oct. 20, 2011

Related U.S. Application Data

(60) Provisional application No. 61/324,556, filed on Apr. 15, 2010.

(51) Int. Cl.
| | | |
|---|---|---|
| *A01N 25/34* | (2006.01) | |
| *A01P 7/04* | (2006.01) | |
| *D01D 5/12* | (2006.01) | |
| *A01N 53/08* | (2006.01) | |
| *A01N 53/00* | (2006.01) | |
| *D01F 1/10* | (2006.01) | |
| *D01F 6/06* | (2006.01) | |

(52) U.S. Cl.
CPC ........ *A01N 53/00* (2013.01); *D01F 1/10* (2013.01); *D01F 6/06* (2013.01)

(58) Field of Classification Search
None
See application file for complete search history.

(56) References Cited

U.S. PATENT DOCUMENTS

| | | | |
|---|---|---|---|
| 4,668,666 A | 5/1987 | Allan et al. | |
| 5,516,815 A | 5/1996 | Buehler et al. | |
| 6,296,865 B1 | 10/2001 | Dujardin et al. | |
| 2002/0136748 A1 | 9/2002 | Bublitz et al. | |
| 2004/0167255 A1* | 8/2004 | Lee et al. | 524/100 |
| 2008/0282624 A1* | 11/2008 | Francis et al. | 52/101 |

FOREIGN PATENT DOCUMENTS

| | | |
|---|---|---|
| DE | 10 2005 054 653 A1 | 5/2007 |
| WO | WO 2005/044001 A2 | 5/2005 |
| WO | WO 2008/004711 A2 | 1/2008 |
| WO | WO 2008/032844 A2 | 3/2008 |
| WO | WO 2009/003468 A1 | 1/2009 |

OTHER PUBLICATIONS

WHO, Deltamethrin, Apr. 2005.*
The e-Pesticide Manual, 13th Edition Version 3.0, deltametherin (223), *Insecticide* IRAC 3;pyrethroid, British Crop Protection Council, Tomlin, England (2003).
Hill, A.R.C., "Annex 1: Characterization the Active Ingredient Release Characteristics of Long-Lasting Insecticidal Mosquito Nets Subjected to Repeated Washing," *Report of the Eleventh WHOPES Working Group Meeting*, United Kingdom (2008).
European Search Report for European Patent Application No. EP 10 15 9994, European Patent Office, Munich, Germany, mailed on Sep. 10, 2010.
International Search Report for International Patent Application No. PCT/EP2011/055838, European Patent Office, Rijswijk, Netherlands, Mailed on Jun. 28, 2011.
English language Abstract of WO2007/054375, corresponding to German Patent Application No. 10 2005 054 653 A1, espacenet database—Worldwide, (2012) (listed as document FP2 on the accompanying form PTO/SB/08A).
Office Action mailed Apr. 25, 2013, in U.S. Appl. No. 13/086,498, inventors Sonneck, R. et al., filed Apr. 14, 2011, U.S. Patent and Trademark Office, Alexandria, VA.
Final Office Action mailed Sep. 16, 2013, in U.S. Appl. No. 13/086,498, inventors, Sonneck, R. et al., filed Apr. 14, 2011, U.S. Patent and Trademark Office, Alexandria, VA.
Office Action mailed May 5, 2014, in U.S. Appl. No. 13/086,498, inventors Sonneck, R. et al., filed Apr. 14, 2011, U.S. Patent and Trademark Office, Alexandria, VA.
Office Action mailed Sep. 21, 2012, in U.S. Appl. No. 12/936,144, inventors Sonneck, R. et al., filed Dec. 20, 2010, U.S. Patent and Trademark Office, Alexandria, VA.
Office Action mailed Apr. 23, 2013, in U.S. Appl. No. 12/936,144, inventors Sonneck, R. et al., filed Dec. 20, 2010, U.S. Patent and Trademark Office, Alexandria, VA.
Office Action mailed Apr. 9, 2014, in U.S. Appl. No. 12/936,144, inventors Sonneck, R. et al., filed Dec. 20, 2010, U.S. Patent and Trademark Office, Alexandria, VA.

* cited by examiner

*Primary Examiner* — Ernst V Arnold
*Assistant Examiner* — Jianfeng Song
(74) *Attorney, Agent, or Firm* — Sterne, Kessler, Goldstein & Fox P.L.L.C.

(57) ABSTRACT

The present invention relates to an insecticide-containing polymeric material containing at least one embedded insecticidally active ingredient in the polymeric matrix and having excellent biological activity, and also to the products produced from this polymer and to their use for protecting humans, animals and plants against arthropods, particularly for controlling insects.

6 Claims, No Drawings

INSECTICIDE-CONTAINING POLYMERIC MATERIAL

The present invention relates to an insecticide-containing polymeric material containing at least one embedded insecticidally active ingredient in the polymeric matrix and having excellent biological activity, and also to the products produced from this polymer and to their use for protecting humans, animals and plants against arthropods, particularly for controlling insects.

It is well known that humans can be protected in their sleep from arthropod stings by insecticide-coated sleeping nets. This is particularly important in countries in which arthropods transmit diseases (malaria for example). Coated fabrics can also be used as drapes in front of windows or doors in order to control arthropods entering dwellings. Similarly, using coated fabrics to cover vegetables or fruits is known as a way of protecting against arthropods. This makes it possible to minimize the contamination with insecticides of the plant parts which are eaten later.

The prior art discloses thermoplastic materials containing insecticidally active ingredients.

The known materials for nets are essentially polyesters, especially polyethylene terephthalate and polyethylene, which, however, only have limited durability (polyester in particular) and partly have surfaces sensed to be unpleasantly brittle to the touch (polyethylene in particular). Therefore, it would be desirable to develop materials based on other, more durable and mechanically more robust polymers.

WO-A2 2008/004711 discloses for example netlike insecticide-containing materials based on polyolefins such as polyethylene and/or polypropylene. Pyrethroids are mentioned as suitable insecticidally active ingredients. The insecticidal material is produced by melt-compounding the thermoplastic polymer with the insecticide and then extruding the material.

WO-A 2008/032844 likewise describes an insect-repelling material obtained by melt-spinning a mixture of insecticide and polyethylene. Pyrethroids are mentioned as possible insecticides.

The use of polypropylene is also known from insecticidal evaporator platelets (for example WO 97/29634, WO 99/01030, WO 05/044001). In insecticidal evaporator platelets, an insecticidally active ingredient is embedded into a polypropylene matrix and quickly released by heating to above 100° C. in order to treat a room for example. A room-temperature use or the use in long-acting materials is not described there, nor a combination with additives.

However, the materials known from the prior art have the disadvantage of satisfying the criteria of the WHOPES directive (see "Guidelines for laboratory and field testing of long-lasting insecticidal mosquito nets", 2005, http://www.who.int/whopes/guidelines/en/) for insecticide-containing long-lasting mosquito nets up to 20 washes only, which means that such materials tend to lose active ingredient at such a high rate that they will have lost their biological activity after just 20 wash cycles or so.

The loss of active ingredient from a textile fabric treated with active ingredient, for example from a net treated with insecticide, can be described in terms of a retention index (see: "Report of the Eleventh WHOPES Working Group Meeting", WHO, HQ, Geneva, 10-13 Dec. 2007, Annex 1). To determine its retention index, the polymeric material is repeatedly subjected to a treatment defined in the WHOPES directive.

According to the WHOPES Phase I directive, the tested textiles shall still have a certain biological activity after they have been subjected to 20 washes. Either knock-down at 60 minutes post-exposure has to be between 95% and 100%, or the mortality at 24 hours post-exposure has to be between 80% and 100%. Knock-down after exposure of mosquitoes to insecticides is considered to be the first visible evidence of the efficacy of an insecticide: the mosquitoes are no longer capable of coordinated movement, flight or walking, and usually fall on their backs without, however, being already dead.

Prior to the treatment and following the treatment, the active-ingredient content of the mixture of polymer and active ingredient is determined. The retention index after n treatments is calculated from the n-th root of active-ingredient content after a treatments divided by active-ingredient content prior to treatment.

Textile fabrics used for vector control desirably have a retention index above 95% in order that there may be sufficient biological activity even after 35 wash cycles. The polymeric insecticide-containing materials known from the prior art have insufficient retention indices (between 50 and 90% after 5 washes) which only ensure efficacy of the material for a comparatively small number of washes and hence for a shorter use life.

There is a further problem in that when deltamethrin is used as active ingredient 2 weeks of storage at 54° C. of the insecticide-containing polymeric material or the nets produced therefrom will witness a conversion of the desired S-α-isomer into the undesired R-α-isomer.

The present invention therefore has for its object to provide novel polymeric, insecticide-containing materials, more particularly based on polypropylene, which exhibit sufficient stability of the active ingredient even after storage, preferably of 2 weeks at 54° C., to ensure sufficient efficacy on the part of the material. It is likewise an object of the present invention to provide an insecticide-containing netlike polymeric fabric which meets the requirements of the above-mentioned WHOPES directive. In addition, the amount of active-ingredient component to be used should be kept as low as possible without compromising the insecticidal effect. Further desiderata are a fast-acting insecticidal effect, a uniform release of active ingredient and also a very simple and inexpensive process of production.

We have found that these objects are achieved by the polymeric insecticide-containing material of the present invention and also by the insecticide-containing netlike polymeric fabrics produced therefrom.

The present invention accordingly provides an insecticide-containing polymeric material containing deltamethrin and also a UV stabilizer, characterized in that the material includes a less than 10%, preferably less then 8% and more preferably less than 6% R-α-isomer fraction of the deltamethrin. It is very particularly preferable for the R-α-isomer fraction to be between 0% and 5%.

The present invention likewise provides a netlike fabric based on the insecticide-containing polymeric material of the present invention.

Such a netlike fabric, containing the polymeric material of the present invention, preferably has in accordance with WILOPES directive (Phase I) a knock-down after 60 minutes of between 95% and 100% or a mortality after 24 hours of between 80% and 100% after at least 25, preferably at least 30 and even more preferably at least 35 washes.

In addition, the netlike fabrics containing the polymeric material of the present invention are characterized in that after at least 5 washes in accordance with the WHOPES report they have a retention index r of the formula (I)

$$r = \sqrt[n]{(t_n/t_0)} \tag{1}$$

where
$t_n$=total active-ingredient content after n washes (g/kg),
$t_0$=total active-ingredient content after 0 washes (g/kg) and
n=number of washes,
of at least 95%.

The netlike fabric containing the polymeric material of the present invention preferably has a regeneration time of less than 24, preferably of less than 8 and more preferably of less than 2 hours (tested in accordance with WHOPES directive (phase 1)).

According to the present invention, the "WHOPES directive" is to be understood as meaning the directive "Guidelines fix laboratory and field testing of long-lasting insecticidal mosquito nets", 2005). This directive is retrievable at the following Internet address: http://www.who.int/whopes/guidelines/en/.

According to the WHOPES directive, a "washing" is defined as follows: a netlike fabric (25 cm×25 cm) is introduced into a 1 liter beaker containing 0.5 liters of deionized water and 2 g/l of "Savon de Marseille" soap (pH 10-11) added just before the netlike fabric and fully dissolved in the deionized water. After addition of the netlike fabric, the beaker is immediately introduced into a warm water bath at 30° C. and shaken for 10 minutes at 155 movements per minute. The netlike fabrics are then removed from the beaker and rinsed twice for 10 minutes at a time with clean, deionized water in the same shaking conditions as mentioned above. Thereafter, the netlike fabrics are dried at room temperature and stored at 30° C. in the dark between the washings.

According to the present invention, the term "knockdown" describes the state of an animal on its back or side, which is still capable of uncoordinated movement up to short, periods of flying.

According to the present invention, the term "mortality" describes an immobile state of an animal on its back or side.

According to the present invention, the term "regeneration time" describes the time which passes until the original efficacy is restored.

Polymeric materials to be used according to the present invention are polypropylene and also polypropylene copolymers. Preference is given to using polypropylene. A multiplicity of polypropylenes are known from the prior art. Polypropylenes can in principle be distinguished according to their manner of synthesis. The main proportion of polypropylenes is produced in the presence of Ziegler-Natta catalysts in the suspension process or more particularly in the so-called gas phase process (cf. Kaiser "Kunststoffchemie für Ingenieure", pages 246 to 254). The gas phase process can also utilize specific catalysts such as metallocenes. The polymers produced using metallocene catalysts are particularly useful as polymeric matrix for the insecticide-containing polymeric material of the present invention. The melting points of polypropylenes produced using metallocene catalysts are usually distinctly below those available using conventional heterogeneous catalyst systems. Defects distributed randomly along the polymer chain cause metallocene polypropylenes, which generally have melting points between 135 and 150° C., to be less capable of crystallizing. The use of metallocenes as catalysts for the synthesis of polypropylenes also permits better stereospecific polymerization, i.e. the tacticity of the polypropylenes and hence their properties are easier to control. Polypropylenes catalysed using metallocenes have a narrower molar mass distribution, i.e. they contain virtually no heptane solubles anymore.

In addition to the type of catalyst used in their synthesis, polypropylenes can also be distinguished according to the spatial arrangement of the side groups of the carbon main chain. There is isotactic polypropylene, atactic polypropylene and syndiotactic polypropylene, although these forms can also occur in mixtures. The insecticide-containing polyolefin material of the present invention preferably utilizes polypropylene having a predominantly isotactic structure.

Polypropylenes can be further distinguished according to their respective areas of use. The properties of the polymers are specifically optimized inter alia for the requirements in injection moulding, in extrusion, in blow moulding, in pressing, in calendering and in melt spinning. The insecticide-containing polymeric material of the present invention preferably utilizes polypropylenes intended for the melt-spinning process to produce filaments, fibres and spunbondeds. Particular preference is given to using polypropylenes useful for the production of multifilament fibres having a low denier of 50 to 150 denier. These are for example polymers bearing the brand names Metocene® and Moplen® (from LyondellBasell, Netherlands), Repol® (Reliance Industries Limited, India), Yuplen® (5K corporation, South Korea), Seetec® (LG Chemical, South Korea) and Achieve® (ExxonMobile Chemical Company, USA). Particular preference is given to metallocene-catalysed polypropylenes, for example Metocene® HM562S, melting temperature 145° C. (from LyondellBasell, Netherlands) and Achieve® 3845 (ExxonMobile Chemical Company, USA).

The polymeric materials used can be produced with the addition of additives which are incorporated into the polymer to stabilize or improve its processing properties. Suitable additives are for example alkylated monophenols, alkylthiomethyl phenols, hydroquinones, tocopherols, hydroxylated thiodiphenyl ethers, alkylidenebisphenols, O-, N- and S-benzyl compounds, hydroxybenzylated malonates, aromatic hydroxybenzyl compounds, triazine compounds, acylaminophenols, esters of β-(3,5-di-tert-butyl-4-hydroxyphenyl) propionic acid with mono- or polyhydric alcohols, esters of β-(5-tert-butyl-4-hydroxy-3-methylphenyl)propionic acid with mono- or polyhydric alcohols, esters of β-(3,5-dicyclohexyl-4-hydroxyphenyl)propionic acid with mono- or polyhydric alcohols, esters of 3,5-di-tert-butyl-4-hydroxyphenyl acetic acid with mono- or polyhydric alcohols, amides of β-(5-di-tert-butyl-4-hydroxyphenyl)propionic acid, ascorbic acid (Vitamin C) and aminic antioxidants. It is likewise possible to use thiosynergists, secondary antioxidants, phosphites and phosphonites.

It is likewise possible to produce the polymeric materials used by using metal deactivators, peroxide scavengers, basic costabilizers, nucleating agents, plasticizers, lubricants, emulsifiers, pigments, viscosity modifiers, catalysts, flow control agents, optical brighteners, flameproofing agents, antistatic agents and blowing agents, benzofuranones and indolinones, fluorescent plasticizers, mould release agents, flame-retardant additives, antistatic agents such as sulphonate salts, pigments and also organic and inorganic dyes and also compounds containing epoxy groups or anhydride groups.

The present invention provides a process for producing the insecticide-containing polymeric material of the present invention, characterized in that first the polymer to be used, preferably polypropylene, deltamethrin and also a UV stabilizer and optionally further insecticides or additives are melted together or separately at temperatures between 120 and 250° C., preferably 150 and 230° C., and subsequently the cooling and solidifying of the polymeric mixture takes place and also the subdivision of the latter into pellets.

In addition to insecticides, it is preferably possible to use UV stabilizers (i.e. UV absorbers and/or light stabilizers) in an amount of 0.01% to 15% by weight, more preferably 0.03% to 8% by weight, based on the total mass of the composition of the insecticide-containing polymeric material. UV absorbers and light stabilizers useful for carrying out the process are for example 2-(2'-hydroxyphenyl)benzotriazoles, 2-hydroxybenzophenones, esters of substituted and unsubstituted benzoic acids, acrylates, nickel compounds, sterically hindered amines, oxamides, 2-(2-hydroxyphenyl)-1,3,5-triazines and also mixtures thereof. Preferably no sterically unhindered amines are used as UV stabilizers, but 2-(2'-hydroxyphenyl)benzotriazoles, 2-hydroxybenzophenones, esters of substituted and unsubstituted benzoic acids, acrylates, nickel compounds, oxamides, 2-(2-hydroxyphenyl)-1, 3,5-triazines and also mixtures thereof are used. Particular preference is given to triazine compounds and butrimezole. Very particular preference is given to phenol, 2-(2H-benzotriazol-2-yl)-6-dodecyl-4-methyl-, branched and linear (CAS 125304-04-3) and 2-(5-chloro-2H-benzotriazol-2-yl)-6-(1,1-dimethylethyl)-4-methylphenol (CAS 3896-11-5).

The polymaterial to be used is for example melted in a single-screw extruder, a twin-screw extruder, a multi-screw extruder or a co-kneader.

The single-screw extruder used can be for example a smooth or grooved barrel extruder or a Transfermix. A grooved barrel extruder is preferred.

Twin-screw extruders may be co- or counter-rotating. Twin-screw extruders may further be close-meshing or non-intermeshing. Preference is given to a close-meshing corotating configuration.

Multi-screw extruders have at least three screws, preferably four to twelve. The screws may each be arranged to form close-meshing pairs, in which case the screw pairs can be arranged tangentially and counter-rotating relative to each other. The screws of a multi-screw extruder can further be all corotating, in which case each screw intermeshes in two neighbouring screws. A special form of multi-screw extruder is the planetary roll extruder wherein a driven central spindle drives freely revolving planetary spindles which in turn circulate in a fixed housing. The central spindle, the planetary spindles and the housings have toothed-wheel intermeshing.

The process of the present invention is particularly preferably carried out using a close-meshing corotating twin-screw extruder.

The construction of the extruder screw is adapted to the respective application scenario.

Room temperature solid insecticides, UV stabilizers and further additives are preferably metered together with the starting polymer pellets into the feed zone of the extruder. In another preferred embodiment, room temperature solid insecticides, UV stabilizers and other additives are melted and metered in liquid form. The extruder housings are temperature controlled to 4 to 250° C. The extruder housing at the feed zone of the extruder is preferably cooled to 4 to 50° C. The remaining extruder housings are preferably temperature controlled to 100 to 250° C. and more preferably to 140 to 250° C. In the extruder, the polymer and, depending on the melting point, the insecticide as well and also the UV stabilizer are melted and mixed. The mixture is extruded through a hole die generally known to a person skilled in the art and pelletized. The additives may also comprise further inorganic or organic fillers such as for example organic pigments, titanium dioxide, carbon black or talcum.

The residence times in which the polymer is liquid during melting and mixing are between 3 and 300 seconds, preferably between 5 and 120 seconds and more preferably between 8 and 30 seconds.

The mixing of the insecticide and of the UV stabilizer and also further additives with the molten polymer can take place in the same apparatus in which the melting of the polymer takes place, or in a further apparatus. All the abovementioned extruders are suitable for the mixing. A further possibility is to mix the insecticide and, where appropriate, the additives with the polymer in a static mixer. The mixing is preferably carried out with a static mixer.

When the insecticide or the additives is added in liquid form, it is generally melted and intermediately stored in an initial charge vessel, from which it is then conveyed into the mixing apparatus. The conveying can be effected for example via a pump or via an increased admission pressure. The temperature of the initial charge vessel is chosen such that the insecticide is stable and the viscosity of the insecticide is sufficiently small to ensure good pumpability. It is advantageous in this case to heat the initial charge vessel, the pump and all lines. The metering into the mixing apparatus preferably proceeds via a needle valve. The metered amount of insecticide is preferably measured by a suitable mass flow rate meter, for example according to the Coriolis principle or according to the heated wire principle, and closed-loop controlled to small deviations via the pump or a valve.

Room temperature liquid insecticides are added to the already molten polymer in a processing zone of the extruder via a needle valve. Depending on the viscosity and melting point of the insecticide, the insecticides, UV stabilizers and other additives or their mixture are heated for this.

After mixing, a preferred embodiment comprises cooling and solidifying of the polymeric materials and also subdivision into pellets. This can be accomplished for example using the common strand pelletization process wherein one or more dies extrude continuous strands which are then air or water cooled to solidify them and subsequently comminuted to the desired size in a pelletizer. Suitable dies are known to a person skilled in the art. Underwater pelletization is a further method, the melt emerging from the die underwater, being cut there and by a circulating blade and subsequently water cooled, thereafter screened off and dried. A further method is water ring pelletization where the polymer is cut in the liquid-melt state in air and thereafter whizzed by centrifugal forces in a rotating water ring to cool. Particular preference is given to the method of underwater pelletization and to the strand pelletization process.

The present invention likewise provides pellets containing the insecticide-containing polymeric material of the present invention.

In one embodiment of the process of the present invention, only polymeric material produced by the mixing operation is fed to a subsequent processing operation. The amount of insecticide in the simple mixing operation is in the range from 0.05% to 15% by weight, preferably in the range from 0.2% to 10% by weight and more preferably in the range from 0.4% to 8% by weight, based on the total mass.

In a further embodiment, a polymeric material having an increased concentration of insecticidally active ingredient is produced in pellet form (known as a masterbatch) and fed to a subsequent processing operation in a mixture with untreated polymer, in this case, the concentration of insecticide in the masterbatch polymeric material of the present invention is increased, preferably to a concentration between 3 to 20% by weight and more preferably 5% to 15% by weight based on the total mass.

A further embodiment comprises a first step of producing the polymeric material of the present invention as a masterbatch which thereafter, by melting and mixing with untreated polymer and possible further additives, is again further processed into a polymeric material of the present invention, which is generated in the form of pellets.

The subsequent processing operation may comprise for example the resulting pellets of the polymeric material of the present invention being processed in a processing step into shaped articles such as for example foils, air-cushioning materials, films, profiles, sheets, wires, threads, tapes, cable and pipe linings, casings for electrical instruments (for example in switchboxes, aircraft, refrigerators, etc.). Preference is given to producing foils in an extrusion operation. These foils can be produced to have one or more layers. A person skilled in the art knows methods whereby multilayered foils can be produced. These include for example coextrusion or lamination. Preference is given to a multilayered foil consisting of one layer of material according to the present invention and also of one or more layers of another material. These other materials can be for example polyethylene (HDPE, LDPE, LLDPE) or polyethylene copolymers, polypropylene, adhesion investigators such as for example ethylene-vinyl acetate copolymer, polyamide, polycarbonate, polyvinyl chloride, polystyrene, polyesters such as for example polyethylene terephthalate qtr polybutylene terephthalate, cellophane, polylactide, cellulose acetate or blends thereof. These polymers can be present in pure form or as blends and may contain additives and further inorganic or organic fillers such as for example organic pigments, titanium dioxide, carbon black or talcum.

It is particularly preferable for the subsequent processing operation to consist in further processing the insecticide-containing polymeric material in a subsequent spinning operation to form fibres, yarns, filaments or threads.

The polymeric material of the present invention preferably utilizes deltamethrin as insecticidally active ingredient. However, it is also possible for further insecticidally active ingredients to be admixed. Suitable additional insecticides are insecticides from the classes of the organophosphates, pyrethroids, neonicotinoids and carbamates.

Organophosphates include for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos(-methyl/-ethyl), coumaphos, cyanofenphos, cyanophos, chlorfenvinphos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, suiprofos, tebupirimfos, temephos, terbufos, tetrachlorvinphos, thiometon, triazophos, triclorfon, vamidothion.

The pyrethroids include for example acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-Cypermethrin, cis-Resmethrin, cis-Permethrin, clocythrin, cycloprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-Fluvalinate, tefluthrin, terallethrin, tetramethrin (-1R-isomer), tralomethrin, transfluthrin, ZXI 8901 and pyrethrin (pyrethrum). Preference according to the present invention is given to beta-cyfluthrin, bifenthrin, cyfluthrin, deltamethrin and transfluthrin. Particular preference according to the present invention is given to beta-cyfluthrin, cyfluthrin, deltamethrin, permethrin (cis-, trans-) and transfluthrin.

The neonicotinoids include for example acetamiprid, clothianidin, dinotefuran, imidacloprid, nitenpyram, nithiazine, thiactoprid and thiamethoxam. Preference according to the present invention is given to imidadoprid and clothianidin.

The carbamates include for example alanycarb, aldicarb, aldoxycarb, allyxycarb, aminocarb, bendiocarb, benfuracarb, bufencarb, butacarb, butocarboxim, butoxycarboxim, carbaryl, carbo-furan, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb and triazamate. Preference according to the present invention is given to bendiocarb and carbaryl.

Further insecticidally active ingredients are for example DDT, indoxacarb, nicotine, bensultap, cartap, spinosad, camphechlor, chlordane, endosulfan, gamma-HCH, HCH, heptachlor, lindane, methoxychlor, acetoprole, ethiprole, fipronil, pyrafitiprole, pyriprole, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluron, chlofluazuron, diflubenzuron, fluazuron, flucycloxuron, flufenoxuron, hexaflumuron, lufenuron, novaluron, noviflumuron, penfluoron, teflubenzuron, triflumuron, buprofezin, cyromazine, diafenthiuron, azocyclotin, cyhexatin, fenbutatin-oxide, chlorfenapyr, binapacryl, dinobuton, dinocap, DNOC, fenazaquin, fenpyroximate, pyrimidifen, pyridaben, tebufenpyrad, tolfenpyrad, hydramethylnon, dicofol, rotenone, acequinocyl, fluacrypyrim, *Bacillus thuringiensis* strains, spirodiclofen, spiromesifen, spirotetramat, 3-(2,5-dimethylphenyl)-8-methoxy-2-oxo-1-azaspiro[4,5]dec-3-en-4-yl ethyl carbonate (alias: carbonic acid, 3-(2,5-dimethylphenyl)-8-methoxy-2-oxo-1-azaspiro[4,5]dec-3-en-4-yl ethyl ester, CAS-Reg.-No.: 382608-10-8), flonicamid, amitraz, propargite, flubendiamide, rynoxapyr, chloranthraniliprol, thiocyclam hydrogen oxalate, thiosultap-sodium, azadirachtin, *Bacillus* spec., *Beauveria* spec., Codlemone, *Metarrhizium* spec., *Paecilomyces spec.*, Thuringiensin, *Verticillium* spec., aluminium phosphid, methylbromide, sulfurylfluorid, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyibutoxid, kaliumoleat, pyridalyl, sulfluramid tetradifon, tetrasul, triarathene and verbutin.

The insecticides mentioned can be used individually or in mixtures.

Preferred insecticides are beta-cyfluthrin, permethrin (cis-, trans-), transfluthrin, bendiocarb, clothianidin, imidacloprid, thiacloprid, ethiprol, fipronil, rynoxapyr, chlorpyriphos-methyl, chlorfenapyr. Particular preference is given to beta-cyfluthrin, transfluthrin, bendiocarb, clothianidin, ethiprol and rynoxapyr.

The concentration of the insecticidally active ingredients in the polymeric material can be varied within a relatively wide concentration range, for example 0.05% to 15% by weight, preferably 0.2% to 10% by weight, more preferably 0.4% to 8% by weight. The concentration shall be chosen according to the field of application such that the requirements concerning insecticidal efficacy, durability and toxicity are met. Adapting the properties of the material can also be accomplished by mixing insecticides in the polymeric material by the blending of materials according to the present invention which contain different insecticides, or by using materials according to the present invention which contain different insecticides which are used in combination with each other, for example as mosaic nets. Custom-tailored textile fabrics are obtainable in this way.

The present invention provides a process for producing filaments, fibres, threads and yarns, characterized in that the insecticide-containing polymeric material of the present invention is initially melted, formed into spun threads and cooled, the spun threads obtained are led through a drawing system and drawn and then optionally the setting of the filaments, fibres, threads and yarns takes place.

In this process, a spin finish is preferably used during the spinning operation.

The threads or filaments are produced, after the mixing operation, by melt spinning as described for example in DE-A 41 36 694 (page 2, lines 27-38, page 5, line 45-page 6, line 23) or DE-A 10 2005 054 653 ([0002]). In this process, the insecticidal polymer produced is melted in a single-screw extruder and forced with the aid of a gear pump through a die plate. The die plate is preceded by a filter pack. The polymer strands emerging from the die plate are subjected to high-speed drawing, spin finishing and winding up.

The melt-spinning process comprises the steps of:
1. preparing the spinning melt
2. melt spinning
3. cooling
4. spin finishing
5. drawing
6. aftertreating The fibres are produced from the molten polymeric material of the present invention using the known melt-spinning processes. Preference is given to processes for producing monofilament fibres, multifilament fibres, fibrous nonwoven webs, hollow fibres, staple fibres, multicomponent fibres and matrix-embedded microfibers. The production of multifilament fibres is particularly preferred.

In step (1), the polymeric material of the present invention, produced by the mixing operation, is melted at temperatures of at least 10° C. below the decomposition temperature and at least 5° C. above the melting point of the polymeric material and conveyed without cooling to the spinnerette die pack. The polymeric material is preferably melted and spun at a temperature below 2513° C., more preferably below 235° C.

Fibre production can be carried out in one stage by the polymeric material being fed to the spinning operation directly after mixing, in molten form. It is similarly possible to carry out a two-stage process wherein the previously produced pellets composed of the above-described polymeric material are melted in a conveyor extruder or in a heatable flask and conveyed to the spin pack.

In a preferred embodiment; the insecticide-containing polymeric material of the present invention is fed to the spinning operation directly after mixing, in molten form.

It is particularly preferable for the insecticide-containing masterbatch polymeric material of the present invention, having an increased insecticide concentration, to be mixed with purely polymer material in the course of the spinning operation. It is preferable for the polymeric material used to be only polypropylene which has been prepared with metallocenes as catalyst. This mixing can be effected in different ways. In one embodiment, the insecticide-containing polymeric material and the additional polymeric material are fed via two separate metering assemblies to the single-screw extruder in which the materials are melted. In a further embodiment, the two polymeric materials are mixed prior to addition into the single-screw extruder and then supplied to the extruder in the form of a premix. In a further embodiment, the insecticide-containing polymer and the unloaded polymeric material are melted in two separate extruders and these two streams of melt are subsequently mixed with each other.

The spinnerette die pack consists of a known construction. The spinnerette die plate can have one to several thousand die holes having hole diameters custom my for fibre production. After the spinnerette die pack, the spun threads pass through a cooling sector, are spin finished and wound up or deposited in cans. The cooling medium used is a liquid or a gas. When it is a liquid, water is used. Dry cooling sectors take the form of quenching chambers in which the spun threads are cooled down with cold air, nitrogen or carbon dioxide being used as cooling gas.

A spin finish is applied to the fibres in the course of the spinning operation. Application of the spin finish modifies the surface properties of the fibres. The spin finish inter alma reduces the friction between metal and thread and between thread and thread, and also reduces the antistatic charging of the fibres. The application of a spin finish is necessary to carry out the melt-spinning operation. Without an appropriate spin finish, the winding and unwinding and further processing of filament yarns is not possible. A person skilled in the art knows how to adapt a spin finish for this purpose. Spin finishes are also known to a person skilled in the art. The amount of the applied nonaqueous constituents of the spin finish is in the range from 0.1% to 2.0% by weight and preferably in the range from 0.5% to 1.5% based on the total mass of the fibre.

The spin finish can be applied at the point of exit from or entry to the fibre production line, the winding/take-off machine, the rewinding machine and/or the quench chamber.

The spin finish, or to be more precise the mixture of spin finish and water, can be applied to the fibre in various ways. In principle, it can be applied by spraying, swapping, rolls, rods and pins.

The spin finish can be meteringly added in one or two or in a plurality of stages.

The wound-up or deposited spun threads can then be led through a drawing system and drawn and wound up as flat filament, or optionally be crimped, set or cut into staple fibres.

Preferably, the spinning and drawing operations are carried out in one system without intermediate winding up of the undrawn filaments. Suitable drawing systems are draw-twist or draw-wind machines for flat multifilaments, compact monofil spin-draw systems for monofilaments, draw production lines and compact spin-draw systems for staple fibres. The drawing systems can be equipped with heatable or partly non-heatable godets or draw rolls, and also guide rollers, further with steam, hot-air and infrared ducts, coating devices, crimping units, dryers, cutting systems and other units. The drawing operation can be followed by any known finishing measure, such as the application of a spin finish or a coating for example.

Setting the filaments or fibres is usually carried out on these systems after the drawing step.

The multifilaments spun at high speed can be draw-textured on machines known for this purpose, and similarly the drawn multifilaments can be textured.

Multifilaments preferred according to the present invention have 1 to 100 filaments, more preferably 5 to 75 filaments and most preferably 10 to 60 filaments.

The present invention further provides threads, yarns, fibres or filaments containing the insecticide-containing polymeric materials of the present invention.

According to the present invention, fibres having a linear density of 1000 to 10 denier, preferably 500 to 20 denier and more preferably 200 to 50 denier are used.

The threads, yarns, fibres or filaments thus produced, containing the polymeric material of the present invention, can subsequently be further processed into any desired products such as for example textile fabrics. Preference is given for example to wovens, braids, knits, felts or nonwovens. Particular preference is given to netlike fabrics such as sleeping nets for example.

The production of wovens and braids is effected by means of two thread systems (warp and weft) crossing each other at right angles. A knitted fabric can be produced from one thread (one-thread knit) or be constructed from two or more threads (warp-thread knit) according to the warp-thread technique. These fabrics are produced on loop-forming or -drawing machines. It is further possible to use short threads or thread pieces to produce felts or nonwovens.

To produce netlike fabrics by means of loop-forming and -drawing processes, it is necessary to produce a so-called warp beam. The polymeric threads are wound in equal length in a parallel arrangement on a bobbin, the so-called warp beam.

To render the polymeric threads more lubricious and robust during processing into a textile fabric, the threads are frequently sized, i.e. coated with a protective film of starch or synthetic sizes. Sizing can be effected using a winding oil which is applied during warp-beam production in order to improve the winding properties during warp-beam production and to reduce thread-on-thread friction and also friction between metal and thread. Reducing friction is important not only for warp-beam production but also for the subsequent loop-forming operation.

Prior to further treatment (for example bleaching and dyeing), textile fabrics composed of manufactured fibres are generally washed, since the manufactured fibres contain small amounts of additives at the fibre surface. These additives comprise more particularly the above-described spin finishes, but other additives such as possibly applied sizes are also removed in the process. This washing operation may be carried out in various ways generally known to a person skilled in the art. In some processes, the washing liquor is agitated, in other fibres the textile fabric moves through the quiescent washing liquor. Possible processes are pulsed washers, jet washers, washing on sieve drums, pad-mangles and also vacuum processes. Continuous processes are preferred on an industrial scale.

In the case of polypropylene and polyethylene fibres, this operation is not carried out in the prior art processes since textile fabrics composed of these polymers cannot be dyed with a dyebath. This holds more particularly for the production of mosquito nets, since in this case the textile fabric is not subjected to any further finishing operation apart from heat setting.

Surprisingly, however, the washing of the netlike fabric of the present invention with water and a detergent prior to the heat-setting step has been found to have a positive effect on the loss of insecticide during washing according to the WHOPES guideline. All the washing processes described above (i.e. pulsed washers, jet washers, washing on sieve drums, pad-mangles and also vacuum processes) can be used for this washing operation.

The fabric thus produced has very elastic properties frequently and is not form stable. In this form, it is more particularly unsuitable for the production of mosquito nets, since this use has specific requirements in terms of shrinkage determined to DIN EN ISO 5077. Therefore, it is preferred to carry out a heat-setting operation. Heat setting can be carried out with hot water, saturated steam or hot air, or in a dry atmosphere. Preference is given to carrying out heat setting in a normal atmosphere without addition of water or steam. Heat setting is preferably carried out using a continuous process in which the textile fabric is fixed on a stenter and led through an oven on a stenter. This oven is preferably subdivided into two or more heating zones which can be individually temperature controlled. During the thermal treatment, the textile fabric can be concurrently subjected to mechanical loading to a varying degree by stretching. This is done by moving the two sides of the stenter apart in the setting oven until the desired width is reached for the formed-loop knit.

The temperature to heat-sot the netlike fabric containing the polymeric material of the present invention is chosen 20° C., preferably 10° C., below the melting temperature of the polymer. Surprisingly, heat setting at a few degrees below the melting temperature of the polymer was found to lead to a reduction in the loss of insecticide during a wash in soapy water.

In addition to the abovementioned netlike fabrics, threads, yarns, fibres or filaments can also be subjected to the washing operation of the present invention and the heat setting of the present invention. These materials also subsequently exhibit the technical effects described in the present invention.

In addition to the surprisingly found effect of the setting temperature on the release of the insecticide from the material of the present invention during washing in accordance with WHOPES directive in soapy water, the setting temperature and the duration of the setting operation which is determined via the speed at which the formed-loop knit is led through the setting over lead to alteration of the crystal structure in the polymer. The crystal structure can be determined using DSC measurements (DSC=Differential Scanning calorimetry (dynamic differential calorimetry)). Differential scanning calorimetry is a measurement method known to a person skilled in the art for determining the crystallinity of polymers. This method determines the amount of heat which needs to be applied for a physical or chemical conversion of a substance. A description of the method can be found inter aha in "Praxis der Thermischen Analyse von Kunststoffen", Ehrenstein, Riedel, Trawiel, Carl Hansen Verlag, Munich 2003. Upon measurement at a heating rate of 10 K/min, the materials of the present invention have only a low proportion of crystal structures that melt above the preferred setting temperature during the DSC measurement under customary conditions.

For example, to produce the netlike fabric of the present invention consisting of the polypropylene HM 562 S from Basell, the duration has to be chosen such that, during a customary DSC measurement at a heating rate of 10 K/min, the amount of crystal structures in the material of the present invention that melts above 140° C. is more than 62 µg and preferably more than 65 J/g.

The present invention insecticide-containing polymeric materials or their descendent products can be successfully used for killing harmful or nuisance arthropods, more particularly arachnids and insects. The netlike fabrics containing the insecticide-containing material of the present invention are preferably used for producing sleeping nets for protection against mosquitoes.

Arachnids include mites (e.g. *Sarcoptes scabiei, Dermatophagoides pteronys-sinus, Dermatophagoides farinae, Dermanyssus gallinae, Acarus siro*) and ticks (e.g. *Ixodes ricinus, Ixodes scapularis, Argas reflexus, Ornithodorus moubata, Boophilius microplus, Amblyomma hebraeum, Rhipicephalus sanguinous*).

Sucking insects include essentially the mosquitoes (e.g. *Aedes aegypti, Aedes albopictus, Aedes vexans, Culex quinquefasciatus, Culex tarsalis, Anopheles gambiae, Anopheles albimanus, Anopheles stephensi, Mansonia titillans*), sand flies (e.g. *Phlebotomus papatasii*), gnats (e.g. *Culicoides furens*), black flies (e.g. *Simulium damnosum*), biting houseflies (e.g. *Sto-moxys calcitrans*), Tsetse flies (e.g. *Glossina morsitans* morsitans), horseflies (e.g. *Taha-nus nigrovittatus, Haematopota pluvialis, Chrysops caceutiens*), common houseflies (e.g. *Musca domestica, Musca autumnalis, Musca vetustissima, Fannia canicularis*), flesh flies (e.g. *Sarcophaga carnaria*), myiasis-causing flies (e.g. *Lucilia cuprina, Chrysomyia chloro-pyga, Hypoderma hovis, Hypoderma lineaturn, Dermatobia hominis, Oestrus ovis, Gasterophilus intestinalis, Cochliomyia hominivorax*), bugs (e.g. *Cimex lectularius, Rhodnius prolixus, Triatoma intestans*), lice (e.g. *Pediculus humanis, Haematepinus suis, Damalina ovis*), fleas (e.g. *Pulex irritans, Xenopsylla cheopis, Ctenocephalides canis, Ctenocephali-des felis*) and sand fleas (*Tunga penetrans*).

Biting insects include essentially cockroaches (e.g. *Blattella germanica, Periplaneta americana, Blatta orientalis, Supella longipalpa*), beetles (e.g. *Sitiophilus granarius, Tenebrio molitor, Dermestes lardarius, Stegobitium paniceum, Anobium punctatum, Hylotrupes bajulus*), termites (e.g. *Reticulitermes lucifugus*), ants (e.g. *Lasius niger, Monomorium pharaonis*), wasps (e.g. *Vespula germanica*) and larvae of moths (e.g. *Eplaestia elutella, Ephestia cautella, Plodia interpunctella, Hofmannophila pseudospretella, Tineola bisselliella, Tinea pellionella, Trichophaga tapetzella*).

The materials of the present invention are preferably used against insects, particularly of the order Diptera and more preferably against the suborder Nematocera.

The present invention likewise provides for the use of the insecticide-containing material of the present invention in the manufacture of textile fabrics such as wovens, braids, knits, felts, nonwovens and/or in the manufacture of netlike fabrics such as sleeping nets, mosquito nets.

The present invention further provides threads, yarns, fibres, filaments; netlike fabrics such as sleeping nets, mosquito nets; textile fabrics such as wovens, braids, knits, felts, nonwovens; extruded parts such as foils, air-cushioning materials, films, profiles, sheets, wires, threads, tapes, cable and pipe linings and casings for electrical instruments.

The present invention further provides an insecticide-containing polymeric material obtainable by the processes described above.

A further embodiment of the present invention protects filaments, fibres, threads and/or yarns obtainable by the processes described above.

EXAMPLES

Test Methods: Biology

Test Insects

Female malaria mosquitoes (*Anopheles gambiae*, sensitive Kisumu strain), fed with sugared water only.

Three-Minute Exposure (Cone Test)

The tests were carried out using WHO standard cones with an exposure time of 3 minutes on part-samples. The net pieces were 30×30 cm in size. In each case, five mosquitoes at a time were placed under one cone and four cones were used on a part-sample. The same sample was subsequently tested once more with four cones and once with two cones, i.e. 2.5 replications involving altogether 50 mosquitoes.

After exposure, the insects were transferred into plastic cups 10 at a time and the knock-down effect was determined after 60 minutes. Knock-down is the first visible indication of the onset of action, and is characterized in that the insects lose coordination of their movements and are no longer able to fly or walk. Thereafter, sugared water was likewise administered and mortality determined after 24 hours. After the tests, the average values were computed.

Washing Operation in Accordance with WHOPES Directive 500 ml of deionized water containing 0.2% (w/v) of laundry detergent (Le Chat, Henkel, France) were introduced at 30° C. into a 1 liter glass bottle. One piece of net 30×30 cm in size or three pieces of net 15×12 cm in size were introduced into the bottle which stood on a horizontal shaker (155 movements per minute) in a water bath at 30° C. Thereafter, the water was poured out of the bottle and the sample was rinsed twice with 500 ml of water each time for 10 minutes again under shaking.

The net samples were line dried for two hours and thereafter additionally for at least 24 hours lying on aluminium foil at 27° C. and 70-80% relative humidity before renewed washing or an evaluation of biological activity.

Analysis of Deltamethin in Polypropylenes

Part A—Sample Preparation:

About 1 g of material of a representative sample (yarn, fabric or pellet) is placed in a 250 ml flask; then approximately 30 ml of xylene (PA quality) are added. The sample material is then dissolved at precisely 3 minutes in an oil bath at 190° C. under reflux (water-cooled column, 20 cm) and stirring (125 revolutions per Minute, magnetic stirrer and stirring bar). The oil bath is removed and about 10 ml of isopropanol (PA quality) are added and the flask is left to cool for about 5 minutes at room temperature to precipitate the polymer. Thereafter the extract is made up with 30 ml of acetonitrile.

The sample is subsequently filtered off with suction (analytical filter, 5 cm diameter) and thereafter the filtrate is passed through a fluted filter (MN 715, 240 mm). Both filtrations are done by washing with 10-20 ml of solvent (acetonitrile) in each case.

Finally, the filtrate is quantitatively transferred into a 100 ml graduated flask and made up with acetonitrile to the calibration mark.

Part B—Quantitative Determination by HPLC Versus External Standard:

The quantification of deltamethrin in samples of polypropylene extracts is carried out by means of HPLC on an Agilent 1100 instrument equipped with a binary pumping system. Deltamethrin and the R-alpha isomer are the target molecules of the analysis. Certified analytical standards are used as reference materials. Separation is carried out under normal phase conditions on a Merck Lichrosorb SI 60 column (5μ particles, dimensions 250×4 mm) at 40° C. column temperature.

The injection volume: is 10 μl (sample preparation see Part A above). Separation is effected by means of a solvent mixture of N-heptane and methyl tertiary-butyl ether (950+50, HPLC quality) at a flow rate of 1 ml per minute. The elution time under these conditions is 10 minutes.

UV detection at a wavelength of 230 nm utilizes a diode array detector. The typical retention time under the conditions described is about 6.3 minutes for the R-α-isomer and 7.0 minutes for the deltamethrin.

Production of Samples:

The polymeric materials of the present invention were produced using a corotating close-meshing twin-screw extruder having a screw diameter of 34 mm and a housing length of 1200 mm. Extruder housing temperature was 200° C. in all steps and extruder speed was 160 rpm. The feed zone of the extruder was cooled with water. The extruder was used to produce a so-called masterbatch having a high concentration of deltamethrin. To this end, 10% by weight of technical grade deltamethrin (BCS AG, Monheim Del.), 2% by weight of Tinuvin® 326 FL (BASF (Ciba), Ludwigshafen, Germany) and 88% by weight of polypropylene (Metocen® HM562S, LyondellBasell, Rotterdam. Netherlands) were mixed in the extruder (TK10). All the materials were supplied in solid form to the feed zone of the extruder. The mixture emerged from the extruder in the form of strands and the strands were cooled in a water bath. Subsequently, the strands were comminuted by pelletization. The pellets contained about 9.2% by weight of deltamethrin.

A second step involved producing threads by diluting about 1.1% by weight of the deltamethrin-containing pellets produced as described above with 98.9% by weight of purely polypropylene (Metocen® HM562S or Yuplen® H 893S (SK Corporation, Seoul, Korea). To this end, the pellets were in each case metered into the feed zone of a single-screw extruder and melted and the two melt streams subsequently combined and mixed. In the course of spinning, about 1% by weight of Stantex® 6051 spin finish (Pulcra Chemicals GmbH, Dusseldorf, Germany) was applied to the fibres. The fibres were subsequently drawn and wound up on bobbins. Fibre thickness was 210 dtex and the fibres consisted of 25 filaments. In the second step, the fibres were drawn down to a thickness of 110 dtex. Three pairs of godets were used for drawing the fibres. The temperature of the pairs of godets was 60, 80 and 120° C. The average tenacity of the fibres was 4.3 cN/dtex and the residual extension of the fibres was 51%.

The two polypropylenes used for dilution differ inter alia in their method of production. Metocen® HM 562S polypropylene was produced using a metallocene catalyst; while Yuplen® H 893S polypropylene was produced using a Ziegler-Natta catalyst.

The polypropylene fibres spun were subsequently used to produce formed-loop knits. To this end, the first step was to produce a warp beam by winding the polypropylene fibres from the individual packages in a parallel arrangement onto one bobbin, the so-called warp beam. These warp beams were subsequently used in a warp-knitting machine to produce the formed-loop knit.

A portion of the untreated formed-loop knit was subsequently subjected to a heat-setting operation on a laboratory scale. This was done using a Mathis DHe 61599 type laboratory steamer. Prior to heat setting, a portion of the pieces of formed-loop knit was washed once. For 1 to 2 net pieces about 35 cm×35 cm in size, 300 ml of 30° C. tap water are admixed with 0.1% of Tween® 20 (Sigma-Aldrich Chemie GmbH, Munich, Germany) and homogenized. A glass rod is used to stir the net pieces therein for 5 min, which are subsequently wrung out and rinsed for 2×1 min with 0.300 ml of dentin water at about 15-20° C. (likewise with stirring). The net pieces are then hung up for at least 1 h to dry. Other pieces of formed-loop knit were subjected to the setting operation in an unwashed state. The setting operation was carried out at different temperatures.

The atmosphere in which the heat setting was carried out was also varied. The heat setting was carried out in a dry atmosphere or in a water vapour saturated atmosphere.

The samples were evaluated in respect of their biological activity and their loss of deltamethrin. This was followed by the repeated performance of the washing procedure of the WHOPES protocol and further evaluations of the biological activity and of the loss of deltamethrin.

RESULTS

1st Example

Influence of Spin-Finish Wash-Off on Biological Activity

In this example, the fibres were produced using exclusively Metocen® HM 562S polypropylene. That is, the dilution of the masterbatch during spinning was done with this polymer. The melting point of Metocen® HM 562S polymer is 145° C., according to its data sheet. Subsequently, the threads were used to produce a formed-loop knit in accordance with the operation described above.

The pieces of formed-loop knit were heat set for 90 seconds in a steam-containing atmosphere at different temperatures. One half of the pieces of formed-loop knit were washed in accordance with the above-described procedure prior to heat setting in order to remove the spin finish from the fibres, while the other half of the pieces of formed-loop knit were not further treated prior to heat setting. The spin finish was still present on the threads of these pieces of formed-loop knit.

The pieces of formed-loop knit were initially tested in respect of their biological activity in accordance with the above-described procedure. Subsequently, the pieces of formed-loop knit were washed in accordance with the above-described washing operation to WHOPES directive for 5, 10, 15, 20, 25 and 30 times in succession and each thereafter evaluated in respect of their biological activity.

TABLE 1

Influence of spin finish on biological activity

| Temperature of heat setting [° C.] | Number of washes to WHOPES protocol [—] | Knock-down after 60 min | | Mortality after 24 h | |
|---|---|---|---|---|---|
| | | Samples washed prior to heat setting | Samples unwashed prior to heat setting | Samples washed prior to heat setting | Samples unwashed prior to heat setting |
| 110 | 0 | 100% | 100% | 100% | 100% |
| 120 | 0 | 100% | 100% | 100% | 100% |
| 130 | 0 | 100% | 100% | 100% | 100% |
| 140 | 0 | 100% | 100% | 100% | 100% |
| 110 | 5 | 100% | 100% | 100% | 100% |
| 120 | 5 | 100% | 100% | 100% | 100% |
| 130 | 5 | 100% | 100% | 100% | 100% |
| 140 | 5 | 100% | 100% | 100% | 100% |
| 110 | 10 | 100% | 95% | 95% | 95% |
| 120 | 10 | 97% | 88% | 97% | 88% |
| 130 | 10 | 98% | 100% | 100% | 100% |
| 140 | 10 | 100% | 98% | 100% | 98% |

TABLE 1-continued

Influence of spin finish on biological activity

| Temperature of heat setting [° C.] | Number of washes to WHOPES protocol [—] | Knock-down after 60 min | | Mortality after 24 h | |
|---|---|---|---|---|---|
| | | Samples washed prior to heat setting | Samples unwashed prior to heat setting | Samples washed prior to heat setting | Samples unwashed prior to heat setting |
| 110 | 15 | 98% | 85% | 94% | 52% |
| 120 | 15 | 96% | 82% | 96% | 53% |
| 130 | 15 | 100% | 89% | 95% | 89% |
| 140 | 15 | 100% | 91% | 100% | 100% |
| 110 | 20 | 100% | 95% | 97% | 84% |
| 120 | 20 | 98% | 95% | 100% | 76% |
| 130 | 20 | 100% | 63% | 100% | 37% |
| 140 | 20 | 100% | 90% | 100% | 95% |
| 110 | 25 | 100% | 88% | 100% | 80% |
| 120 | 25 | 95% | 80% | 95% | 59% |
| 130 | 25 | 98% | 80% | 93% | 78% |
| 140 | 25 | 100% | 88% | 98% | 93% |
| 110 | 30 | 95% | 85% | 100% | 89% |
| 120 | 30 | 96% | 70% | 96% | 54% |
| 130 | 30 | 100% | 83% | 100% | 90% |
| 140 | 30 | 100% | 93% | 95% | 98% |

The results show that washing the spin finish off prior to heat setting achieves a significantly better biological effect after 15 washes to WHOPES directive.

The samples washed prior to heat setting display a clear relationship between the temperature chosen for the heat setting and the biological activity. The closer the temperature to the melting point of the polymer, the higher the biological effect.

The temperature at heat setting must accordingly be at most 20° C. and preferably at most 10° C. below the melting temperature of the polymer in order that a maximum biological activity is achieved.

2nd Example

Effect of Spin-Finish Wash-Off on Deltamethrin Loss

Example 2 used the same formed-loop knits whose production was described in Example 1. The samples were investigated in respect of their deltamethrin content according to the procedure described above.

TABLE 2

Loss of deltamethrin

| Temperature of heat setting [° C.] | Number of washes to WHOPES protocol [—] | Deltamethrin content | | Retention index | |
|---|---|---|---|---|---|
| | | Samples washed prior to heat setting | Samples unwashed prior to heat setting | Samples washed prior to heat setting | Samples unwashed prior to heat setting |
| 110 | 0 | 100% | 100% | | |
| 120 | 0 | 100% | 100% | | |
| 130 | 0 | 100% | 100% | | |
| 140 | 0 | 100% | 100% | | |
| 110 | 5 | 64% | 32% | 91.4% | 79.4% |
| 120 | 5 | 69% | 38% | 92.8% | 82.3% |
| 130 | 5 | 79% | 51% | 95.3% | 87.4% |
| 140 | 5 | 82% | 34% | 96.0% | 80.4% |
| 110 | 10 | 53% | 26% | 93.8% | 87.2% |
| 120 | 10 | 57% | 30% | 94.5% | 88.7% |
| 130 | 10 | 63% | 39% | 95.5% | 91.1% |
| 140 | 10 | 84% | 54% | 98.2% | 94.0% |
| 110 | 15 | 52% | 22% | 95.8% | 90.4% |
| 120 | 15 | 59% | 30% | 96.5% | 92.3% |
| 130 | 15 | 61% | 34% | 96.8% | 93.0% |
| 140 | 15 | 79% | 50% | 98.5% | 95.4% |
| 110 | 30 | 43% | 23% | 97.2% | 95.2% |
| 120 | 30 | 49% | 23% | 97.6% | 95.2% |
| 130 | 30 | 53% | 28% | 97.9% | 95.8% |
| 140 | 30 | 63% | 39% | 98.5% | 96.9% |

The deltamethrin content after heat setting was set equal to 100% and the pieces of formed-loop knit were subsequently analysed for their deltamethrin content after 5, 10, 15 and 30 washes in accordance with the WHOPES protocol.

The results show that temperature at heat setting must be at most 20° C. and preferably at most 10° C. below the melting temperature of the polymer to minimize the loss of deltamethrin from the formed-loop knit of the present invention.

3rd Example

Influence of Spin-Finish Wash-Off on Active-Ingredient Stability During Storage

Example 3 used the same formed-loop knits whose production was described in Example 1. The samples were investigated, directly after production, with regard to active-ingredient stability following 2 weeks' storage at 54° C. These storage conditions were used to simulate a minimum shelf-life of 2 years. Storage took place in a Heraeus Thermo Scientifics B620 drying oven. The temperature of 54° C. was constantly monitored. The net samples were packed for storage in 2 to 4 layers in aluminium foil.

The samples were stored at 54° C. for 2 weeks and then analysed for their deltamethrin R-α-isomer content in accordance with the method described above:

TABLE 3

Fraction of R-α-isomer after storage

| Temperature at heat setting [° C.] | R-α-isomer of deltamethrin | |
|---|---|---|
| | Samples unwashed prior to heat setting | Samples washed prior to heat setting |
| 110 | 50.74% | 5.07% |
| 120 | 43.58% | 5.68% |
| 130 | 45.74% | 4.66% |
| 140 | 51.11% | 5.42% |

The results show that washing off the spin finish can be used to reduce the formation of R-α-isomer during storage to below 10%.

4th Example Influence of Atmosphere

Example 4 used the same formed-loop knits whose production was described in Example 1. The table which follows shows the influence of the atmosphere at heat setting on the loss of deltamethrin during the performance of washes according to the WHOPES directive. The pieces of formed-loop knit were all heat set at 140° C. for 90 seconds. In the process, the atmosphere was varied in the setting oven. Half the pieces of formed-loop knit were heat set in a standard atmosphere without added water or steam (dry atmosphere), while the other pieces of formed-loop knit were heat set in a standard atmosphere in the presence of steam.

TABLE 4

Influence of atmosphere at heat setting

| Atmosphere [—] | Number of washes to WHOPES protocol [—] | Deltamethrin content [%] |
|---|---|---|
| Steam | 0 | 100% |
| Dry | 0 | 100% |
| Steam | 5 | 82% |
| Dry | 5 | 90% |
| Steam | 10 | 84% |
| Dry | 10 | 86% |
| Steam | 15 | 79% |
| Dry | 15 | 81% |
| Steam | 30 | 63% |
| Dry | 30 | 69% |

The results show that when a dry atmosphere is used during heat setting the loss of deltamethrin during the washes to WHOPES directive is less.

5th Example

Influence of Polypropylene Type on Biological Activity

In this example, the fibres were produced using Metocen® HM 562S polypropylene and Yuplen® H 893S polypropylene, i.e. during spinning the masterbatch was in each case diluted with one of these polymers. Subsequently, the threads were used to produce a formed-loop knit in accordance with the operation described above.

The pieces of formed-loop knit were heat set in a dry atmosphere for 90 seconds at different temperatures. Prior to heat setting, the pieces of formed-loop knit were washed in accordance with the procedure described above in order to remove the spin finish present on the fibres.

After heat setting, the samples of formed-loop knit were subjected to 20 washes in accordance with the WHOPES directive and tested in respect of their biological activity as described above.

TABLE 5

Influence of polypropylene type on biological activity after 20 washes

| Temperature of heat setting [° C.] | Knock-down Yuplen ® H 893S | Knock-down Metocen ® HM562S | Mortality Yuplen ® H 893S | Mortality Metocen ® HM562S |
|---|---|---|---|---|
| 70 | 90% | 98% | 74% | 98% |
| 90 | 64% | 98% | 66% | 100% |
| 110 | 85% | 98% | 90% | 100% |
| 120 | 86% | 95% | 74% | 93% |
| 130 | 100% | 100% | 100% | 100% |
| 140 | 100% | 100% | 100% | 100% |

The results show that a higher biological activity is achieved when a polypropylene produced using a metallocene catalyst is used than when a polypropylene produced using a Ziegler-Natta catalyst is used.

6th Example

Influence of Different UV Stabilizers on Isomerization of Deltamethrin

The polymeric materials of the present invention were produced using a corotating close-meshing twin-screw extruder having a screw diameter of 34 mm and a housing length of 1200 mm. Extruder housing temperature was 200° C. in all steps and extruder speed was 160 rpm. The feed zone of the extruder was cooled with water. Total throughput was 20 kg/b.

In a first step, polymer pellets having a concentration of 2% by weight of deltamethrin were produced. To this end, 2% by weight of technical grade deltamethrin (BSC AG, Monheim Del.) and 98% by weight of polypropylene (Metocen® HM4562S, LyondellBasell, Rotterdam, Netherlands) were mixed in the extruder. All the materials were supplied in solid form to the feed zone of the extruder. The mixture emerged from the extruder in the form of strands and the strands were cooled in a water bath. Subsequently, the strands were comminuted by pelletization.

In the second step, polymer pellets containing 1% or 5% by weight of UV stabilizer were produced. To this end, 1% by weight or 5% by weight of the UV stabilizer and 99% or 95% by weight, respectively, of polypropylene (Metocen® HM562S, LyondellBasell, Rotterdam, Netherlands) were mixed in the extruder. All the materials were supplied in solid form to the feed zone of the extruder. The mixture emerged from the extruder in the form of strands and the strands were cooled in a water bath. Subsequently, the strands were comminuted by pelletization.

In the third step, the two previously produced pellet products comprising deltamethrin or UV stabilizer were mixed with polypropylene in the extruder such that a nominal concentration of 1% by weight of deltamethrin and a 0.2% by weight concentration of UV stabilizer were obtained (TK1). To this end, 50% of the pellet product comprising deltamethrin, 20% or 4% of the pellet product comprising UV stabilizer and, respectively, 30% or 46% polypropylene were mixed in a tumble mixer and this mixture was extruded using a corotating close-meshing twin-screw extruder under the abovementioned conditions. The pellet mixture was supplied in solid form to the feed zone of the extruder. The mixture emerged from the extruder in the form of strands and the strands were cooled in a water bath. Subsequently, the strands were comminuted by pelletization. The pellets contained about 0.9% by weight of deltamethrin.

The polymeric material of the present invention was used to produce films having a thickness of about 50 µm. To this end, the polymeric material was initially dried at 30° C. for 4 to 17 h. Subsequently, it was melted in a single-screw extruder and extruded through a film slot die. The temperature of the single-screw extruder was varied between 220 and 250° C. The extruded films were withdrawn using a polishing stack. The temperature of the first roll of the polishing stack was about 85° C. and the temperature of the second roll of the polishing stack was about 60° C.

The following UV stabilizers were used in the tests:

TABLE 6

UV stabilizers

| Trade name | Manufacturing company | Chemical class |
|---|---|---|
| Chimasorb ® 2020 | BASF (Ciba), Ludwigshafen, Germany | 1,6-Hexanediamine, N,N'-bis(2,2,6,6-tetramethyl-4-piperidinyl) polymer with 2,4,6-trichloro-1,3,5-triazine, reaction products with N-butyl-1-butanamine and N-butyl-2,2,6,6-tetramethyl-4-(CAS 192268-64-7)piperidinamine |
| Tinuvin ® 326 | BASF (Ciba), Ludwigshafen, Germany | Bumetrizole, 2-(5-chloro-2H-benzotriazole-2-yl)-6-(1,1-dimethylethyl)-4-methylphenol (CAS 3896-11-5) |
| Tinuvin ® 571 FF | BASF (Ciba), Ludwigshafen, Germany | Triazine compound, phenol, 2-(2H-benzotriazol-2-yl)-6-dodecyl-4-methyl-, branched and linear (CAS 125304-04-3) |
| Tinuvin ® 783 FDL | BASF (Ciba), Ludwigshafen, Germany | Poly[[6-[(1,1,3,3-tetramethyl-butyl)amino]-1,3,5-triazin-2,4-diyl][(2,2,6,6-tetramethyl-4-piperidinyl)imino]-1,6-hexanediyl[(2,2,6,6-tetramethyl-4-piperidinyl)imino]]), (CAS 71878-19-8), butanedioic acid, dimethylester, polymer with 4-hydroxy-2,2,6,6-tetramethyl-1-piperidine ethanol (CAS 65447-77-0) |

The films were subsequently analysed for their deltamethrin content using the abovementioned analytical methods:

TABLE 7

R-α-isomer content

| UV stabilizer | Extrusion temperature [° C.] | Deltamethrin (DLT) content [% by weight] | R-☐-isomer content [% of DLT] |
|---|---|---|---|
| Chimasorb ® 2020 | 220 | 0.859 | 9.989 |
| Chimasorb ® 2020 | 240 | 0.883 | 12.503 |
| Chimasorb ® 2020 | 250 | 0.888 | 14.496 |
| Tinuvin ® 326 | 220 | 0.986 | 0.785 |
| Tinuvin ® 326 | 240 | 0.979 | 0.000 |
| Tinuvin ® 326 | 250 | 0.931 | 0.868 |
| Tinuvin ® NOR 571 FF | 220 | 0.879 | 2.471 |
| Tinuvin ® NOR 571 FF | 240 | 0.906 | 3.713 |
| Tinuvin ® NOR 571 FF | 250 | 0.944 | 4.677 |
| Tinuvin ® 783 FDL | 220 | 0.871 | 8.999 |
| Tinuvin ® 783 FDL | 240 | 0.861 | 10.858 |
| Tinuvin ® 783 FDL | 250 | 0.882 | 12.154 |

The results show that no sterically hindered amines may be used for UV stabilization in order that isomerization of more than 10% of the deltamethrin may be prevented in the course of the further processing of the polymeric materials of the present invention.

7th Example

Prior Art: Coated PET Nets

The insecticide-laden Permanet net from Vestergaard Frandsen S. A., Switzerland was evaluated with respect to biological activity and deltamethrin content. This was followed by repeated performance of the washing procedure according to the WHOPES protocol and further evaluations of biological activity and deltamethrin loss.

The deltamethrin content of the net was determined in the same way as described for the polypropylene net.

TABLE 8

Deltamethrin content and retention index

| Number of washes to WHOPES protocol [—] | Knock-down after 60 min | Mortality after 24 h | Deltamethrin (DLT) content [% by weight] | Retention index [—] |
|---|---|---|---|---|
| 0 | 100 | 100 | 0.208 | 0 |
| 5 | 100 | 100 | 0.086 | 84% |
| 10 | 98 | 100 | 0.066 | 89% |
| 15 | 97 | 84 | 0.059 | 92% |
| 20 | 84 | 72 | 0.050 | 93% |
| 25 | 69 | 64 | 0.040 | 94% |
| 30 | 70 | 61 | 0.042 | 95% |

The insecticide-laden Permanet net from Vestergaard Frandsen S.A., Switzerland was tested for active-ingredient stability after 2 weeks' storage at 54° C. These storage conditions are used to simulate a minimum shelf life of 2 years. The samples were stored at 54° C. for 2 weeks and subsequently analysed for their deltamethrin R-α-isomer content in accordance with the method described above. A double determination was carried out.

TABLE 9

R-α-isomer content
R-α-isomer of DLT

| Before 2 weeks' storage at 54° C. | After 2 weeks' storage at 54° C. |
|---|---|
| 3.35% | 47.44% |
| 3.51% | 35.35% |

The results show that this commercially available net meets the WHO requirements in respect of knock-down and mortality for 15 washes only and has a retention index of less than 95% after 5 washes. Furthermore, the R-α-isomer content after 2 weeks' storage at 54° C. is distinctly more than 30%.

8th Example

Prior Art: PE Nets

The insecticide-laden nets Netprotect® (BESTNET EUROPE LTD., Britain) and Duranet® (Clarke Products, USA) were evaluated with respect to biological activity. This was followed by repeated performance of the washing procedure to the WHOPES protocol and further evaluations of biological activity.

TABLE 10

Biological activity

| Number of washes to WHOPES protocol [—] | Netprotect ® | | Duranet ® | |
|---|---|---|---|---|
| | Knock-down after 60 min [%] | Motorality after 24 h [%] | Knock-down after 60 min [%] | Mortality after 24 h [%] |
| 0 | 100 | 100 | 100 | 100 |
| 5 | 93 | 83 | 100 | 98 |
| 10 | 66 | 44 | 100 | 98 |

TABLE 10-continued

| Number of washes to WHOPES protocol [—] | Biological activity | | | |
|---|---|---|---|---|
| | Netprotect ® | | Duranet ® | |
| | Knock-down after 60 min [%] | Motorality after 24 h [%] | Knock-down after 60 min [%] | Mortality after 24 h [%] |
| 15 | 19 | 57 | 95 | 95 |
| 20 | 7 | 14 | 64 | 70 |
| 25 | n.d. | n.d. | 64 | 70 |
| 30 | n.d. | n.d. | 51 | 51 |
| 35 | n.d. | n.d. | 41 | 41 | n.d. = not determined.

The results clearly show that the commercially available nets tested, which are based on polyethylene as fibre material, no longer meet the WHOPES directive in respect of biological activity after distinctly fewer than 35 washes.

The invention claimed is:

1. An insecticide-containing polymeric material comprising a polymer, deltamethrin, and a UV stabilizer, wherein the material comprises a less than 10% R-α-isomer fraction of the deltamethrin, and wherein the UV stabilizer is selected from the group consisting of branched or linear 2-(2H-benzotriazol-2-yl)-6-dodecyl-4-methyl phenol, and 2-(5-chloro-2H-benzotriazol-2yl)-6-(1,1-dimethylethyl)-4-methylphenol and wherein the polymer is polypropyjene or a polypropylene copolymer.

2. The insecticide-containing polymeric material according to claim 1, wherein the polypropylene is produced using metallocenes as a catalyst.

3. A process for producing the insecticide-containing-polymeric material according to claim 1, comprising
first melting the polymer, deltamethrin, the UV stabilizer, and optionally further insecticides or additives together or separately at a temperature of between 120 and 250° C.,
subsequently cooling and solidifying the polymeric mixture, and
subdividing the solidified polymeric mixture into pellets.

4. The insecticide-containing polymeric material according to claim 1 wherein the material is in the form of pellets.

5. The insecticide-containing polymeric material according to claim 1, wherein the UV stabilizer is branched or linear 2-(2H-benzotriazol-2-yl)-6-dodecyl-4-methyl phenol.

6. The insecticide-containing polymeric material according to claim 1, wherein the UV stabilizer is 2-(5-chloro-2H-benzotriazol-2yl)-6-(1,1-dimethylethyl)-4-methylphenol.

* * * * *